United States Patent [19]

Smith et al.

[11] Patent Number: 5,164,121
[45] Date of Patent: Nov. 17, 1992

[54] POURABLE COMPOSITION CONTAINING AN AMINE OXIDE -POLYETHYLENE GLYCOL MIXTURE

[75] Inventors: Kim R. Smith; James E. Borland; Joe D. Sauer, all of Baton Rouge, La.

[73] Assignee: Ethyl Corporation, Richmond, Va.

[21] Appl. No.: 749,683

[22] Filed: Aug. 26, 1991

Related U.S. Application Data

[62] Division of Ser. No. 525,984, May 21, 1990, abandoned.

[51] Int. Cl.$^5$ .................... C07C 291/00; C11D 1/75; C11D 3/20; C11D 17/08
[52] U.S. Cl. .................................. 252/547; 252/117; 252/118; 252/134; 252/174.21; 252/DIG. 5; 252/DIG. 14; 252/DIG. 16; 564/297; 564/298; 564/299
[58] Field of Search ............... 252/117, 118, 528, 547, 252/153, 174.21, DIG. 14; 564/297, 298, 299

[56] References Cited

U.S. PATENT DOCUMENTS

| 4,176,080 | 11/1979 | Wise | 252/170 |
| 4,264,466 | 4/1981 | Carleton | 252/174.21 |
| 4,276,205 | 6/1981 | Ferry | 252/547 |
| 4,793,943 | 12/1988 | Haslop | 252/174.19 |
| 4,830,782 | 5/1989 | Broze | 252/545 |

FOREIGN PATENT DOCUMENTS

59-164396  9/1984  Japan ................... 252/547

*Primary Examiner*—Dennis Albrecht
*Attorney, Agent, or Firm*—Patricia J. Hogan

[57] ABSTRACT

A pourable amine oxide composition which is suitable for use in detergent compositions is obtained by reacting a tert-amine with aqueous hydrogen peroxide in a normally liquid polyethylene glycol as the sole organic solvent. When the composition has a low water content, it is suitable for use in water-sensitive formulations, such as bar soaps and detergent concentrates.

7 Claims, No Drawings

POURABLE COMPOSITION CONTAINING AN AMINE OXIDE -POLYETHYLENE GLYCOL MIXTURE

This application is a division of application Ser. No. 525,984, filed May 21, 1990 now abandoned.

FIELD OF INVENTION

This invention relates to amine oxide compositions and more particularly to such compositions suitable for incorporation into water-sensitive detergent formulations and to processes for preparing them.

BACKGROUND

As disclosed in Kirk-Othmer, *Encyclopedia of Chemical Technology*, Third Edition, Volume 2, pp. 259–271, it is known that amine oxides which are useful in various applications, such as detergent and shampoo formulations, can be prepared by reacting non-heterocyclic tert-amines with aqueous hydrogen peroxide in a solvent such as water, a lower alcohol, acetone, or acetic acid.

Copending application Ser. No. 415,910 (Smith et al.), filed Oct. 2, 1989, teaches that it is also possible to prepare the amine oxides as solid, non-hygroscopic dihydrates by conducting their syntheses in organic solvents, such as esters, hydrocarbons, and highly polar solvents, in which the products are soluble at reaction temperatures but insoluble at a lower temperature.

These amine oxides, which are generally trialkylamine oxides, particularly trialkylamine oxides containing both short and long alkyl groups, are sometimes utilizable as prepared. However, the solid amine oxides present handling problems; and the solvents used in the known syntheses of amine oxides, especially the flammable solvents and water, are apt to be undesirable in some applications. Moreover, even when not undesirable because of making a harmful contribution, such as an excess of water in a water-sensitive formulation, the solvents have the unattractive feature of contributing weight and bulk to amine oxide-containing formulations without serving a useful purpose therein.

It would be advantageous to be able to provide amine oxide compositions which could be poured or pumped from the vessels in which they are prepared to combine them with other ingredients of formulations in which they are to be incorporated, e.g., water-sensitive formulations, without having them in conjunction with solvents that would serve no useful function in the formulations and could be deleterious.

U. S. Pat. No. 3,565,810 (Mausner et al.) shows a recognition of some of these problems and an attempt to solve them, but its process uses so much water that its products have too much unnecessary bulk and weight and would not be suitable for incorporation into water-sensitive formulations.

SUMMARY OF INVENTION

It has now been found that compositions having a high surfactant content can be obtained by conducting at least the latter part of the reaction of a tert-amine with aqueous hydrogen peroxide to form an amine oxide in the presence of a normally liquid polyethylene glycol.

It has also been found that the use in the process of a fairly highly concentrated hydrogen peroxide solution and/or the removal of at least a portion of the water from the final reaction mixture can provide a pourable liquid blend of a tert-amine oxide and a solvent consisting essentially of a normally liquid polyethylene glycol and 0–30% by weight of water, a blend which is suitable for easy incorporation into water-sensitive formulations, such as bar soaps and detergent compositions.

DETAILED DESCRIPTION

The amine used in the practice of the invention may be any tert-amine that can be oxidized to a tert-amine oxide with aqueous hydrogen peroxide. Such amines are well known and include a variety of tert-amines having aliphatic, cycloaliphatic, and/or aromatic groups attached to the amino nitrogen. However, they are generally trialkylamines corresponding to the formula $RR'R''N$ wherein R, R', and R'' are primary alkyl groups containing 1–30 carbons, preferably such trialkylamines in which R is methyl or ethyl, R' is an alkyl group containing 6–20 carbons, and R'' is independently selected from methyl, ethyl, and alkyl groups containing 6–20 carbons.

Exemplary of the tert-amines that may be used are trimethylamine, triethylamine, N-isobutyldimethylamine, trihexylamine, N,N-dimethyl-2-ethylhexylamine, N-eicosyldimethylamine, N-isobutyl-N-triacontylmethylamine, N-benzyldimethylamine, Nethyldibenzylamine, N,N-diisobutyl-4-t-butylbenzylamine, tri-2hydroxyethylamine, N-dodecyldi-2-hydroxyethylamine, N,N-didecyl2-hydroxyethylamine, and, more preferably, the N-alkyldimethyl-, N-alkyldiethyl-, N-alkyl-N-ethylmethyl-, N,N-dialkylmethyl-, and N,N-dialkylethylamines in which the alkyl groups are hexyl, octyl, decyl, dodecyl, tetradecyl, hexadecyl, octadecyl, and/or eicosyl, as well as mixtures of such amines.

The aqueous hydrogen peroxide which is reacted with the tert-amine may have a concentration of 1–99% by weight but, in a preferred embodiment of the invention, has a concentration or 50–70% by weight. The more dilute solutions are apt to contribute more water to the product than is desired in many instances, but the excess water may be removed from the product after completion of the reaction in those instances.

As in conventional tert-amine/hydrogen peroxide reactions, the amount of hydrogen peroxide employed should be at least the stoichiometric amount but generally not more than a 15% molar excess; and the reaction is conducted by adding the aqueous hydrogen peroxide to the amine, preferably at a controlled rate and preferably in the presence of carbon dioxide or a chelating agent, such as diethylenetriaminepentaacetic acid or ethylenediaminetetraacetic acid, at a temperature of about 20°–100° C., preferably 60°–80° C.; and the reaction temperature is maintained for 1–24 hours.

The process of the invention differs from the conventional processes in that at least the latter part of the reaction is conducted in the presence of a normally liquid polyethylene glycol as the sole organic solvent. Although the presence of such a solvent in the initial reaction mixture would not prevent the reaction from occurring, it is generally preferred to initiate the reaction in the absence of the organic solvent and then to add it gradually during the reaction so as to maintain the reaction mixture stirrable and/or so as to provide an amine oxide/polyethylene glycol weight ratio of about 0.1–10/1 in the final reaction mixture.

The polyethylene glycol solvent employed in the process is one that is normally liquid, i.e., a polyethylene glycol or mixture of polyethylene glycols having average molecular weights such as to be liquid at ambient temperature.

After completion of the reaction, the reaction mixture may be cooled to room temperature and, if necessary, then reheated to a fluidizing temperature when the reaction mixture is not fluid and it is desired to be able to pour or pump the reaction product from the vessel in which it was prepared. Alternatively, the reaction product may be poured or pumped from the reaction vessel before the temperature has been reduced to a point at which the product is no longer fluid when it is a product that is apt to gel at lower temperatures.

The amine oxide solution formed by the process contains water because of the use of the aqueous hydrogen peroxide. Since a small amount of water can be tolerated even in water-sensitive formulations in which it might be desired to incorporate the amine oxide, and the solutions containing relatively large amounts of water can be used in formulations which are not water-sensitive, it may not be necessary to remove any of the water in the solution. However, when the solution contains more water than is desired, it is removed from the reaction product by conventional means. The removal of the water may sometimes be accomplished by ordinary distillation, but the relatively low decomposition temperatures of some of the amine oxides makes it preferable to remove the water under reduced pressure to minimize the possibility of decomposing the product. Vacuum stripping is a particularly preferred method of removing at least a portion of the water from the product.

The invention is advantageous in that it provides amine oxide compositions having a high surfactant content that makes them attractive for incorporation into detergents, not only because of their surfactant content but because of their being pourable or pumpable. Moreover, the compositions having low water contents have those advantages as well as an ability to be used in water-sensitive formulations, such as bar soaps and detergent concentrates; and the use of the polyethylene glycol serves to enhance the viscosity of personal care formulations instead of decreasing the viscosity as the use of an aqueous or alcoholic solvent would.

The following example is given to illustrate the invention and is not intended as a limitation thereof.

EXAMPLE

A suitable reaction vessel was charged with 100 g of N-tetradecyldimethylamine and 0.5 g of diethylenetriaminepentaacetic acid. After the mixture was heated to 65° C. under a carbon dioxide atmosphere, 23 g of 70% hydrogen peroxide (a 15% molar excess) was added over a period of five minutes while cooling to prevent the temperature from rising further. The temperature was then raised to 75° C. and held there for approximately seven hours while adding a polyethylene glycol having a molecular weight below 1000 as needed to facilitate stirring. By the end of the seven hours, a total of 55 mL of the polyethylene glycol had been added, and the amine conversion was greater than 95%. The product was liquid at ambient temperature.

We claim:

1. A pourable liquid blend consisting of a surfactant tert-amine oxide; a normally liquid polyethylene glycol solvent, and 0–30% of water, based on the weight of the blend wherein the amine oxide/polyethylene glycol weight ratio is in the range of about 0.1-10/1.

2. The blend of claim 1 containing not more than about 25% by weight of water.

3. The blend of claim 2 containing not more than about 10% by weight of water.

4. The blend of claim 1 wherein the tert-amine oxide is a compound corresponding to the formula RR'R"NO in which R, R', and R" are primary alkyl groups containing 1-30 carbons.

5. The blend of claim 4 wherein R is methyl or ethyl, R' is an alkyl group containing 6-20 carbons, and R" is independently selected from methyl, ethyl, and alkyl groups containing 6-20 carbons.

6. The blend of claim 5 wherein R and R" are methyl.

7. The blend of claim 6 wherein the tert-amine oxide is N-tetradecyldimethylamine oxide.

* * * * *